(12) United States Patent
Leganza et al.

(10) Patent No.: US 8,420,808 B2
(45) Date of Patent: Apr. 16, 2013

(54) PROCESS FOR THE PREPARATION OF EFAVIRENZ

(75) Inventors: Alessandro Leganza, Alte Di Montecchio Maggiore (IT); Marco Galvagni, Alte Di Montecchio Maggiore (IT)

(73) Assignee: F.I.S. Fabbrica Italiana Sintetici S.p.A., Alte di Montecchio Maggiore (IT)

( * ) Notice: Subject to any disclaimer, the term of this patent is extended or adjusted under 35 U.S.C. 154(b) by 174 days.

(21) Appl. No.: 13/060,839

(22) PCT Filed: Jan. 30, 2009

(86) PCT No.: PCT/EP2009/000612
§ 371 (c)(1),
(2), (4) Date: Feb. 25, 2011

(87) PCT Pub. No.: WO2010/085978
PCT Pub. Date: Aug. 5, 2010

(65) Prior Publication Data
US 2011/0196151 A1   Aug. 11, 2011

(51) Int. Cl.
*C07D 265/12* (2006.01)

(52) U.S. Cl.
USPC ............................................. 544/92; 544/90

(58) Field of Classification Search .............. 544/92
See application file for complete search history.

(56) References Cited

FOREIGN PATENT DOCUMENTS
WO    WO 98/45278 A1   10/1998

OTHER PUBLICATIONS
M.E. Pierce et al., "Practical Asymmetric Synthesis of Efavirenz (DMP 266), an HIV-1 Reverse Transcriptase Inhibitor", Journal of Organic Chemistry, vol. 63, pp. 8536-8543 (1998).

*Primary Examiner* — Kahsay T Habte
(74) *Attorney, Agent, or Firm* — Dickstein Shapiro LLP

(57) ABSTRACT

The present invention is directed to a process for the preparation of Efavirenz, (4S)-6-chloro-4-(cyclopropylethynyl)-4-(trifluoromethyl)-1,4-dihydro-2H-3,1-benzoxazin-2-one, of formula (I)

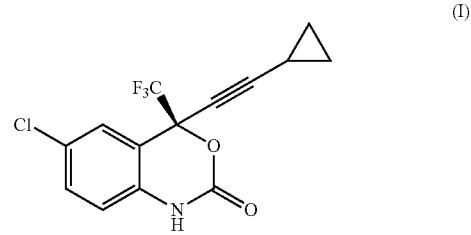

comprising reacting the intermediate of formula (II) [0045]

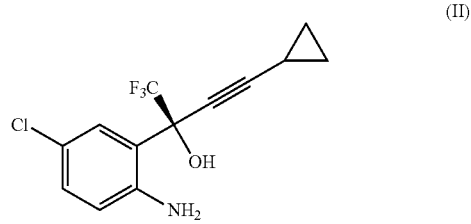

as a free base or a salt thereof, with diphosgene (TCMCF, trichlormethylchloroformate) Cl3CO—COCl in an organic solvent or in a biphasic medium comprised of an organic solvent and water, preferably but not mandatorily in the presence of a weak base in an amount sufficient to neutralise the reaction mixture or in an up to 30% molar excess of such amount.

21 Claims, No Drawings

PROCESS FOR THE PREPARATION OF EFAVIRENZ

TECHNICAL FIELD OF THE INVENTION

The present invention is directed to a process for the preparation of Efavirenz.

BACKGROUND ART

Efavirenz is a well known non-nucleoside reverse transcriptase inhibitor (NNRTI) that is used in the antiretroviral therapy of HIV-1. Efavirenz is on the market for this use since 1998.

Several processes are known in the prior art to produce this active substance that start from the intermediate of formula (II):

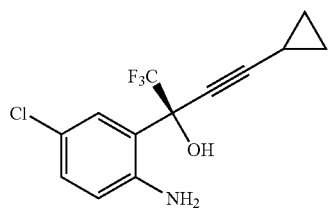

(II)

This intermediate, (2S)-2-(2-amino-5-chlorophenyl)-4-cyclopropyl-1,1,1-trifluorobut-3-yn-2-ol, as a free base, is reacted with a chloroformate derivative in basic conditions to give, after 1 to 6 hours reaction, an alkyl carbamate intermediate (reaction of the amine moiety of intermediate (II) with the chloroformate derivative) that is then cyclized to yield Efavirenz.

Even if this kind of reaction allows to obtain Efavirenz with an acceptable impurities profile, it has some disadvantages due to the length of the reaction time and/or the quite complicate work-up, as the alkyl carbamate intermediate must be isolated or the reaction mixture must be at least separated and concentrated before undergoing the cyclization step.

No one-step process using chloroformate derivatives has been proposed so far, nor thrichloromethylchloroformate (diphosgene) has been proposed as a reactant of choice in this process.

BRIEF DESCRIPTION OF THE INVENTION

It has now been surprisingly found that by reacting intermediate (II) with diphosgene in pretty neutral or slightly basic conditions, it is possible to obtain Efavirenz with a one-step process in a short time and with high yield and purity.

DETAILED DESCRIPTION OF THE INVENTION

A process is provided for the preparation of Efavirenz, (4S)-6-chloro-4-(cyclopropylethynyl)-4-(trifluoromethyl)-1,4-dihydro-2H-3,1-benzoxazin-2-one, of formula (I):

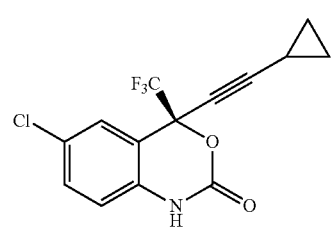

(I)

comprising reacting the intermediate of formula (II):

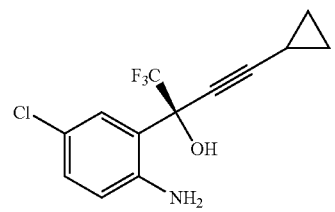

(II)

as a free base or a salt thereof, with diphosgene (TCMCF, trichloromethylchloroformate) $Cl_3CO—COCl$ in an organic solvent or in a biphasic medium comprised of an organic solvent and water.

Preferably, the said reaction is performed in the presence of a weak base in an amount sufficient to neutralise the reaction mixture or in an up to 30% molar excess of such amount.

If a salt of intermediate of formula (II) is used, such a salt is preferably a mesylate salt. In this case, intermediate (II) salt is provisionally treated with a basic medium for a time sufficient to obtain the free base, before adding the diphosgene reagent.

More preferably, the inventive process is performed starting from intermediate (II) free base. This allows to obtain Efavirenz with an improved purity profile.

Intermediate (II) free base can be obtained by treating a salt of intermediate (II) such as mesylate salt—intermediate (II). 1,5 methansulphonic acid—with a base such as an hydroxide of an alkaline metal in an aqueous solution. The reaction can be performed in an organic solvent at room temperature, as will be described in the experimental part of the present description.

The reaction of intermediate (II) free base to give Efavirenz can be performed without isolating the said intermediate, but just separating the organic layer containing the free base from the previous step and subjecting it to the subsequent step of reaction with diphosgene.

The diphosgene has a formula $Cl_3CO—COCl$ and thus it can deliver two moles of phosgene per mole, according to the following reaction:

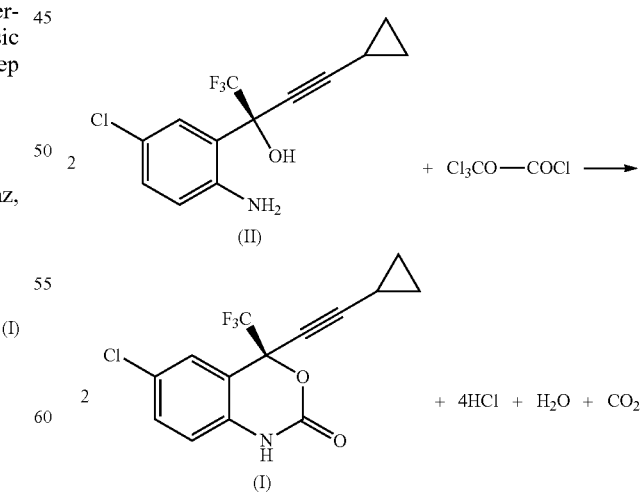

It can be used a stoichiometric amount of diphosgene or a slight excess up to a 30% molar excess, more preferably a 20 to 25% molar excess.

As said above, this reaction can be performed in an organic solvent such as, for example but not limited thereto, an hydrocarbon selected from hexane, heptane and the like, an ether selected from diethylether, diisopropylether, tetrahydrofuran, dioxane and the like, chloroform, dichloromethane and the like, or a mixture of such solvents. More preferably, however, the reaction is conducted in a biphasic medium comprised of an organic solvent such as the one listed above and water. If the weak base is an inorganic base, water helps to solve the weak base and to promote the reaction.

The ratio between the organic solvent and the water phase can range between 0.3:1 to 1:0.3.

Preferably, the organic solvent is a mixture of tetrahydrofuran and heptane in a ratio of between 0.8:1 and 1:0.8, more preferably about 1:1.

As said above, the reaction can be performed in the presence of a weak base. Such a weak base is preferably an inorganic weak base such as a carbonate or a hydrogencarbonate of an alkaline or earth-alkaline metal. It should be noted that the weak base has the function to capture hydrogen chloride that is delivered by the reacting diphosgene, according to the reaction scheme shown above, and not to catalyse the reaction. Therefore, the amount of weak base will depend on the amount of diphosgene used and will be an amount sufficient to keep the reaction medium neutral, that is about the stoichiometric amount with respect to the amount of diphosgene, or up to 30% molar excess amount.

In a very preferred embodiment of the invention, the weak base is sodium hydrogencarbonate.

The reaction can be performed at temperatures chosen in the range from 0° C. to 50° C., preferably 10° C. to 40° C., more preferably 18° C. to 30° C., even more preferably at around room temperature.

The reaction is accomplished by adding diphosgene to the reaction mixture containing intermediate (II) free base in an organic solvent or a biphasic medium as described above containing the said weak base. It has been surprisingly found that the purity profile of the final product Efavirenz can be improved if such an addition is made in a short time, the only limit being just the exothermal behavior of the reaction, in order to operate in the temperature ranges depicted above.

This allows the reaction to complete in a very short time, namely less than 1 hour, more particularly between 20 and 40 minutes. Typically, in about 30 minutes the reaction is complete.

It has also been surprisingly found that the purity profile of the reaction can be further enhanced if ammonia is added before the work-up of the reaction mixture. As $NH_3$ reacts with diphosgene to give urea, it avoids that residual thrichloromethylchloroformate could remain in the product. Typically, aqueous ammonium hydroxide is used.

Diphosgene can be prepared by known methods of photochloruration (use of chlorine gas under irradiation) starting from methyl chloroformate $CH_3O$—COCl. It has been seen that the presence of dichloromethyl chloroformate in a too high amount is detrimental to the purity of Efavirenz. It is therefore preferable that the amount of dichloromethyl chloroformate in diphosgene is not higher than 0.3% by weight, as detected by GC/TCD chromatography.

Also the presence of residual chlorine in diphosgene can promote the formation of impurities in the subsequent reaction to give Efavirenz. Therefore, it is preferable that the color characteristics of diphosgene (which is a measure of the amount of chlorine present in the substance) is classified as GY4 score.

To obtain diphosgene with such a color characteristics, it is possible to degasing diphosgene, for example by bubbling nitrogen in diphosgene at 60-70° C. for about 4 hours.

It is also preferable that Efavirenz contains no more than 10 ppm of p-chloroaniline (determined by HPLC), as this substance is classified cancerogenic. This can be accomplished by using intermediate (II) wherein p-chloroaniline is comprised in no more than 200 ppm (determined by HPLC).

The invention will be now further described by means of illustrative examples that are not intended to limit the scope of protection as defined by the appended claims.

EXPERIMENTAL PART

Preparation

Intermediate (II) Free Base

In a 30 l glass lined reactor the following substances were charged under nitrogen atmosphere:

2.0 kg of intermediate (II). 1,5 methansulphonic acid;
3.5 l of THF;
3.5 l of heptanes;
7.0 l of purified water.

The mixture was stirred by keeping the temperature at 15-25° C. The pH was adjusted to >9 with about 690 ml of 30% NaOH in water (1.5 eq).

The mixture was stirred at 20-25° C. until a clear solution was observed (two clear phases), then the layers were separated.

Example

Reaction of Intermediate (II) Free Base to Efavirenz

To the organic phase containing intermediate (II) as free base as prepared above, an aqueous solution of 9.6 kg of 10% $NaHCO_3$ (0.75 eq) was added. The resulting biphasic suspension was stirred by keeping the temperature at 15-25° C.

To said mixture, 560 g of diphosgene (0.615 eq) were added and the biphasic solution was stirred at 20-25° C. for at least 10 minutes, then an "in process" control was carried out.

When the reaction was complete (about 30 minutes) 140 ml (0.45 eq) of 30% $NH_4OH$ aqueous solution were added. The resulting solution was stirred for at least 1 hour, then the two phases were separated.

To the organic phase 7.0 l of heptanes were added and the resulting mixture was washed twice with 3.5 l of purified water each, while keeping the temperature at 40-50° C. Then, the solution was treated with 100 g of charcoal, the dark slurry was aged at 40-50° C. for at least 30 minutes, then filtered in a SS filter. The exhausted charcoal was washed with 3.0 l of THF/heptanes (1:1 in volume).

The organic solution was distilled under reduced pressure at 60-70° C. in a 30 l glass lined reactor to give a residual 6.0 l volume. To the obtained slurry 15.8 l of heptanes were added, then it is re-distilled under reduced pressure at 60-70° C. to a residual 8.0 l volume. Further 13.8 l of heptanes were added and the THF content was checked by GC to be less than 0.1%.

The obtained suspension was added with 220 ml of THF and the resulting slurry was heated to 70-80° C. until a clear solution was observed, then the temperature was allowed to reach 48-52° C.

The solution was seeded with 4 g of Efavirenz Form 1; the suspension was stirred by keeping the temperature at 40-50°

C. for at least 1 hour, then it was cooled in about 2 hours to −5/−20° C. and stirred at this temperature for 1 hour.

The slurry was then filtered and the wet cake was washed for three times at −5/−20° C. with 3.0 l of heptanes each.

The solid was dried in stove under vacuum at 85° C. for at least 8 hours, obtaining a weight dry product of 1350 g.

The final product was obtained in a 93% yield and a HPLC purity higher than 99.8%.

By comparison, Efavirenz obtained according to the prior art method disclosed in WO 98/34928 has a HPLC purity of 96%, while Efavirenz synthesized as described in WO 06/029079 was obtained in a 78-90% yield.

The invention claimed is:

1. Process for the preparation of (4S)-6-chloro-4-(cyclopropylethynyl)-4-(trifluoromethyl)-1,4-dihydro-2H-3,1-benzoxazin-2-one, of formula (I):

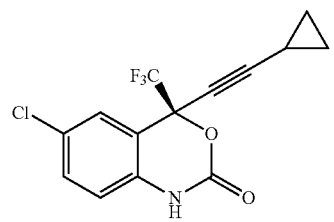

(I)

comprising reacting the intermediate of formula (II):

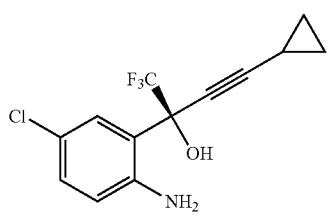

(II)

as a free base or a salt thereof, with diphosgene of formula $Cl_3CO$—$COCl$ in an organic solvent or in a biphasic medium comprised of an organic solvent and water.

2. Process according to claim 1, wherein the said reaction with diphosgene is performed in the presence of a weak base in an amount sufficient to neutralise the reaction mixture or in an up to 30% molar excess of such amount.

3. Process according to claim 1, wherein, if a salt of intermediate of formula (II) is used, such a salt is a mesylate salt and wherein intermediate (II) salt is provisionally treated with a basic medium obtain the free base, before adding the diphosgene reagent.

4. Process according to claim 1, further comprising a step of preparation of intermediate (II) free base.

5. Process according to claim 4, wherein the said intermediate (II) free base is obtained by treating a salt of intermediate (II) with a base such as an hydroxide of an alkaline metal as an aqueous solution in an organic solvent at room temperature.

6. Process according to claim 4, wherein the reaction of intermediate (II) free base to give Efavirenz is performed without isolating the said intermediate (II), by subjecting the organic layer containing intermediate (II) free base to the subsequent step of reaction with diphosgene.

7. Process according to claim 1, wherein the diphosgene is used in stoichiometric amount or in a slight excess up to a 30% molar excess.

8. Process according to claim 1, wherein the reaction is performed in a biphasic medium comprising an organic solvent selected from an hydrocarbon selected from hexane, heptane, an ether selected from diethylether, diisopropylether, tetrahydrofuran, dioxane, chloroform, dichloromethane, or a mixture of such solvents and water.

9. Process according to claim 8, wherein the ratio between the organic solvent and the water phase can range between 0.3:1 to 1:0.3.

10. Process according to claim 8, wherein the organic solvent is a mixture of tetrahydrofuran and heptane in a ratio of between 0.8:1 and 1:0.8.

11. Process according to claim 1, wherein said weak base is an inorganic weak base, in an amount that is about the stoichiometric amount with respect to the amount of diphosgene, or an up to 30% molar excess amount.

12. Process according to claim 11, wherein the said weak base is sodium hydrogencarbonate.

13. Process according to claim 1, wherein the said reaction is performed at temperatures chosen in the range from 0° C. to 50° C., or in the range from 10° C. to 40° C., or in the range from 18° C. to 30° C., or at around room temperature.

14. Process according to claim 13, wherein diphosgene is added to the reaction mixture containing intermediate (II) free base in an organic solvent or a biphasic medium and the said weak base, in the shortest time that allows the temperature to be maintained in the range from 0° C. to 50° C., or in the range from 10° C. to 40° C., or in the range from 18° C. to 30° C., or at around room temperature.

15. Process according to claim 1, wherein ammonia or aqueous ammonium hydroxide is added before the work-up of the reaction mixture.

16. Process according to claim 1, wherein the said diphosgene contains an amount of dichloromethyl chloroformate not higher than 0.3% by weight, as detected by GC/TCD chromatography.

17. Process according to claim 1, wherein the color characteristics of said diphosgene are classified as GY4 score.

18. Process according to claim 1, wherein the said intermediate (II) comprises p-chloroaniline in no more than 200 ppm amount, as determined by HPLC.

19. Process according to claim 7, wherein the diphosgene is used in a 20 to 25% molar excess.

20. Process according to claim 10, wherein the mixture of tetrahydrofuran and heptane is in a ratio of about 1:1.

21. Process according to claim 11, wherein said weak base is a carbonate or a hydrogencarbonate of an alkaline or earth-alkaline metal.

* * * * *